(12) United States Patent
Kamphuis

(10) Patent No.: US 11,850,302 B2
(45) Date of Patent: Dec. 26, 2023

(54) COLLAGEN CHEW

(71) Applicant: TotumVos LLC, Keene, NH (US)

(72) Inventor: Suzanna Lynn Kamphuis, Keene, NH (US)

(73) Assignee: Totum Vos LLC, Keene, NH (US)

( * ) Notice: Subject to any disclaimer, the term of this patent is extended or adjusted under 35 U.S.C. 154(b) by 308 days.

(21) Appl. No.: 17/096,232

(22) Filed: Nov. 12, 2020

(65) Prior Publication Data

US 2021/0145738 A1 May 20, 2021

Related U.S. Application Data

(60) Provisional application No. 62/935,383, filed on Nov. 14, 2019.

(51) Int. Cl.

| | | |
|---|---|---|
| *A61K 9/00* | (2006.01) | |
| *A61K 31/198* | (2006.01) | |
| *A61K 38/39* | (2006.01) | |
| *A61K 47/42* | (2017.01) | |
| *A61K 47/46* | (2006.01) | |
| *A61K 47/24* | (2006.01) | |
| *A23L 33/17* | (2016.01) | |
| *A23L 33/115* | (2016.01) | |
| *A23L 33/105* | (2016.01) | |
| *A23P 30/10* | (2016.01) | |
| *A61K 47/44* | (2017.01) | |

(52) U.S. Cl.
CPC .......... *A61K 9/0056* (2013.01); *A23L 33/105* (2016.08); *A23L 33/115* (2016.08); *A23L 33/17* (2016.08); *A23P 30/10* (2016.08); *A61K 31/198* (2013.01); *A61K 38/39* (2013.01); *A61K 47/24* (2013.01); *A61K 47/42* (2013.01); *A61K 47/44* (2013.01); *A61K 47/46* (2013.01); *A23V 2002/00* (2013.01)

(58) Field of Classification Search
CPC . A23V 2250/5432; A23L 33/18; A23L 33/17; A23L 33/105; A23L 33/115; A61K 8/64; A61K 9/0056; A61K 9/0058
See application file for complete search history.

(56) References Cited

U.S. PATENT DOCUMENTS

2020/0138704 A1* 5/2020 Wan ..................... A61K 31/155

* cited by examiner

*Primary Examiner* — Hong T Yoo
(74) *Attorney, Agent, or Firm* — Maine Cernota & Curran

(57) ABSTRACT

A chewable supplement made by providing gelatin; providing an optional emulsifier; providing a food-grade oil; mixing the gelatin, and the emulsifier with the food-grade oil with to achieve a first mixture; heating the first mixture to achieve a heated first mixture; removing heat from the first mixture; providing collagen; adding the collagen to the first mixture and mixing the collagen with the first mixture to achieve a collagen mixture; and separating the collagen mixture into individual doses.

14 Claims, 4 Drawing Sheets

100

105

SINGLE CHEW

200

205

WRAPPED CHEW

PACKAGED CHEWS

METHOD

COLLAGEN CHEW

RELATED APPLICATIONS

This application claims the benefit of U.S. Provisional Application No. 62/935,383, filed Nov. 14, 2019. This application is herein incorporated by reference in its entirety for all purposes.

FIELD OF THE INVENTION

The invention relates to chewable dietary supplements, and more particularly, to a chewable, non-sticky collagen ingestible.

BACKGROUND OF THE INVENTION

The health benefits of collagen are widely recognized. Collagen is recommended for healthy hair and nails, and it can benefit the elderly as well as athletes such as runners, endurance athletes, and weight lifters. The form in which it is administered can impact its absorption and the ease with which a user might administer it. Similarly, benefits may require specific dosages hard to administer through known powders and chewable items. Administration may be especially difficult for users for whom swallowing or chewing might be difficult. A consistency that is too sticky or too hard would be difficult for those with dentures or with weakened teeth or mandibles. Chews must also be shelf stable and transportable so as not to require special storage or handling.

What is needed, therefore, are techniques for providing a desired dose of collagen in non-sticky and soft chews.

SUMMARY OF THE INVENTION

An embodiment provides a system for the delivery of collagen, the system comprising a chew, the chew comprising a non-sticky gelatinous composition of matter, the matter comprising: a gelatin base; an emulsifier if the chew comprises a water-based liquid; a food grade oil; and powdered collagen. Embodiments further comprise at least one additional ingredient from the group consisting of baobab powder, cocoa butter, coconut milk, and sea salt. Other embodiments further comprise at least one flavoring selected from the list consisting of coffee, chocolate, mocha, citrus, chai, chai-beet, turmeric, and herbal. In subsequent embodiments the collagen has a collagen weight, the gelatin base comprises gelatin, the gelatin has a gelatin weight, and there exists a collagen weight to gelatin weight ratio wherein the collagen weight to gelatin weight ratio is between approximately 6 and approximately 13.

Another embodiment provides a chewable supplement, the chewable supplement comprising gelatin; collagen; medium-chain triglyceride (MCT) oil; and an emulsifier if the chew comprises a water-based liquid. For additional embodiments, the gelatin and the collagen each has a weight ratio between 1:5 and 1:15. For additional embodiments the emulsifier is lecithin. In another embodiment, the chewable supplement comprises approximately 600 mg of the gelatin, approximately 6,000 mg of the collagen, approximately 460 mg of the medium-chain triglyceride oil, and approximately 76 g of the emulsifier. A following embodiment further comprises sea salt; baobab; and an emulsion. In subsequent embodiments the emulsion is coconut milk. Additional embodiments further comprising C-complex; cocoa butter; monk fruit extract; and stevia. Included embodiments further comprise chai concentrate, wherein the chai concentrate is a brewed liquid comprising a liquid base, ginger, cinnamon, peppercorns, cardamom, and cloves; and beet root. Yet further embodiments further comprise coffee; and cacao. Related embodiments further comprise lemon concentrate; water; lemon oil; and turmeric. Further embodiments further comprise coffee concentrate; and cacao. Ensuing embodiments further comprise at least one additional ingredient from the group consisting of blueberry-lavender, chamomile flavoring, and an L-Theanine calming supplements.

A yet further embodiment provides a method for making a chewable supplement, the method comprising providing gelatin; providing an emulsifier if the chewable supplement comprises a water-based liquid; providing a food-grade oil; mixing the gelatin, and the emulsifier with the food-grade oil with to achieve a first mixture; heating the first mixture to achieve a heated first mixture; removing heat from the first mixture; providing collagen; adding the collagen to the first mixture; mixing the collagen with the first mixture to achieve a collagen mixture; and separating the collagen mixture into individual doses. For yet further embodiments separating the collagen mixture into the individual doses is selected from the group consisting of pouring the collagen mixture into a molding apparatus, chilling the collagen mixture in the molding apparatus, releasing the collagen mixture from the molding apparatus, and cutting the collagen mixture into the individual doses, and rolling the collagen mixture out onto a surface and cutting the collagen mixture into the individual doses. For more embodiments, the first mixture is heated in a double-boiler. In continued embodiments the chewable supplement is a chill chew, and the method further comprises chilling the collagen mixture.

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposes, and not to limit the scope of the inventive subject matter.

DETAILED DESCRIPTION

Figure 1:
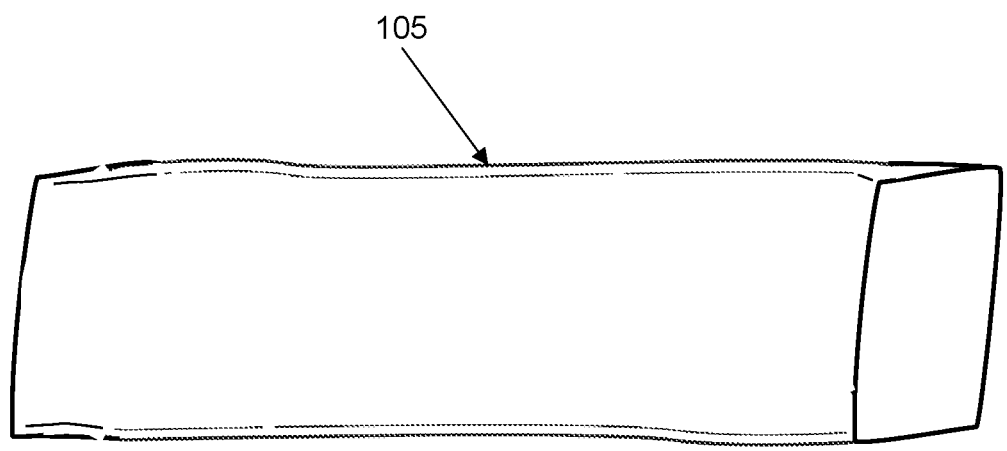
FIG. 1 depicts a chew in accordance with one embodiment of the present invention.

FIG. 1, 100 depicts a chew 105.

Figure 2:
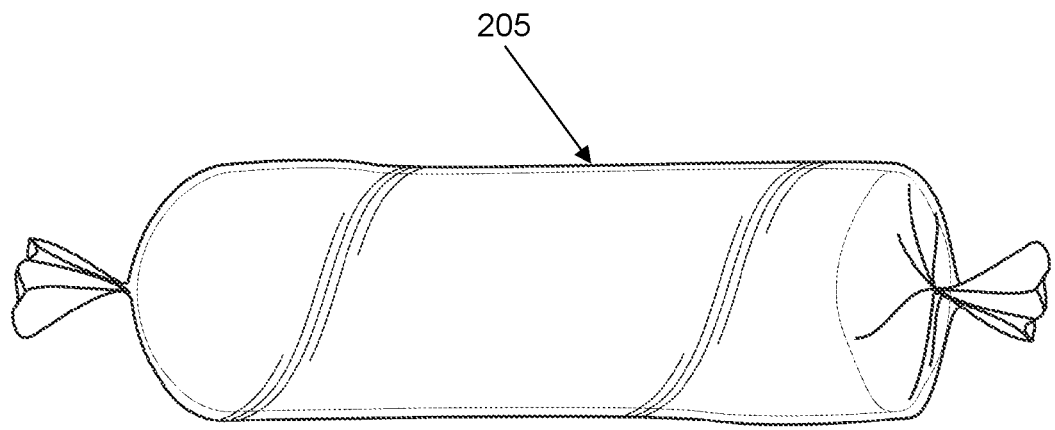
FIG. 2 depicts a wrapped chew in accordance with one embodiment of the present invention.

FIG. 2, 200 depicts a wrapped chew 205. In embodiments the chew is a rectangular cuboid, frozen in a sheet pan (at the point) and cut from there, and wrappers are made from non-plastic, natural cellophane.

Figure 3:
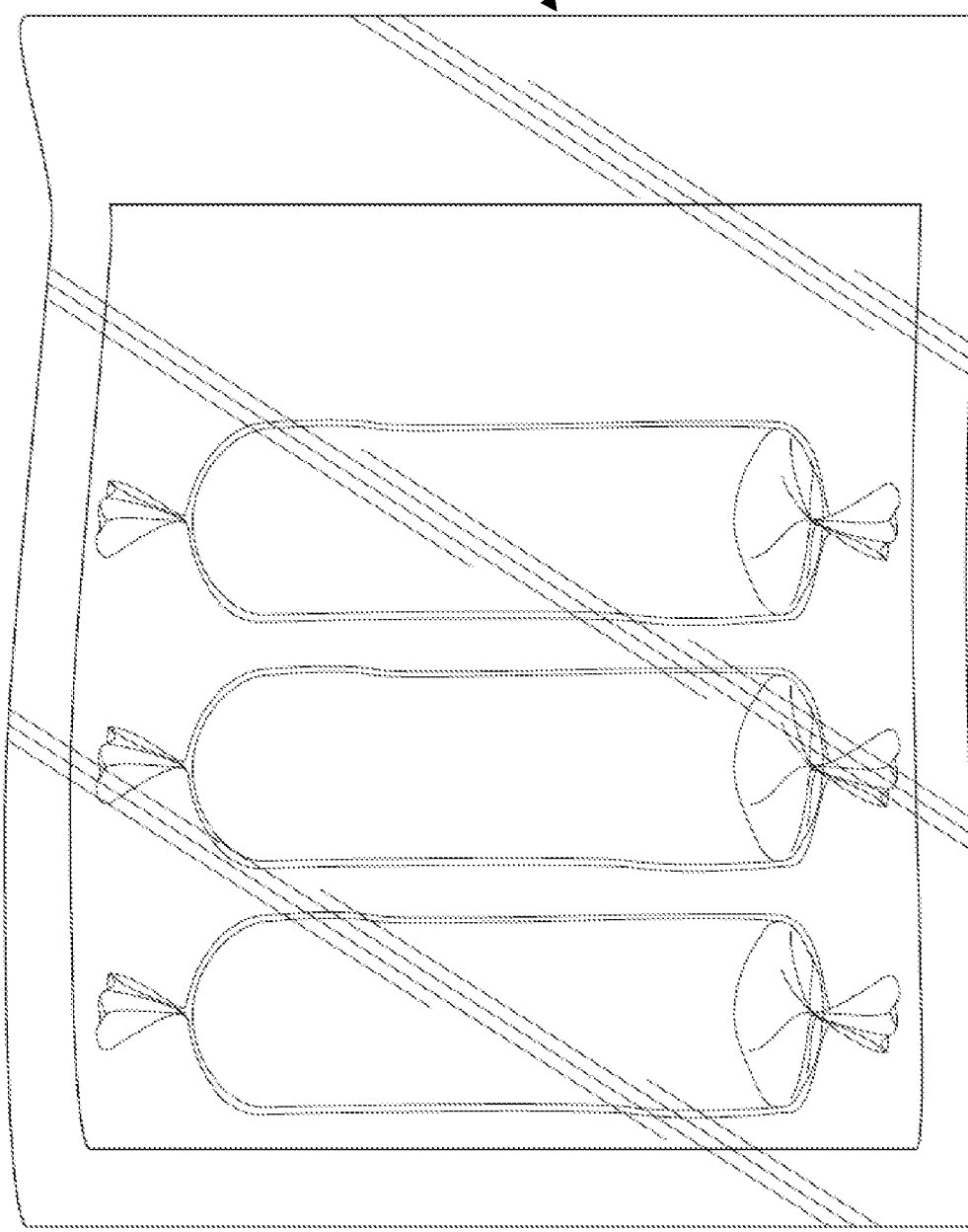
FIG. 3 depicts packaged chews in accordance with one embodiment of the present invention.

FIG. 3, 300 depicts packaged chews 305.

Figure 4:
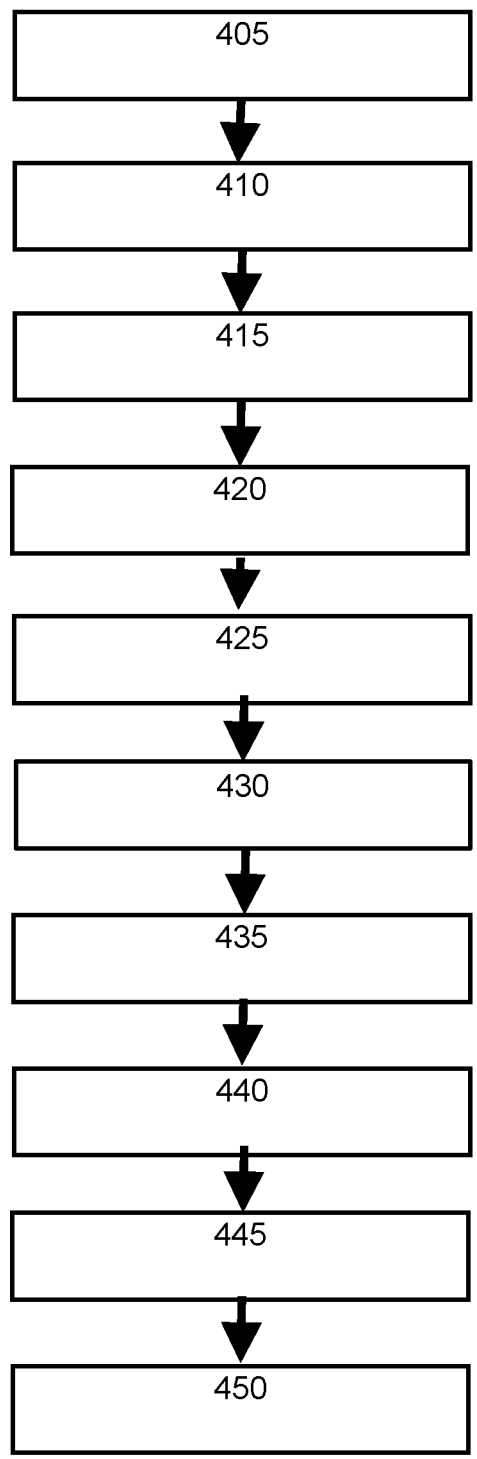
FIG. 4 is a flowchart for a method for making a chew in accordance with one embodiment of the present invention.

FIG. 4 is a flowchart 400 of a method for making a chewable supplement. The method comprises providing gelatin 405; providing an emulsifier 410; providing a food-grade oil 415; mixing the gelatin and the emulsifier with the food-grade oil to achieve a first mixture 420; heating the first mixture to achieve a heated first mixture 425; removing heat from the first mixture 430; providing collagen 435; adding the collagen to the first mixture 440; mixing the collagen with the first mixture to achieve a collagen mixture 445; and separating the collagen mixture into individual doses 450.

One embodiment provides a chew comprising an emulsified and gelatinous base wherein 6,000 mg of collagen is incorporated. Other doses may be incorporated based on a variety of therapeutic or health factors. Various flavors may be added to the chew to improve taste for the user. Examples of flavorings that may be added include, but are not limited to, chai seasonings, blueberry-lavender, mocha and coffee flavors, turmeric, citrus flavors, herbs, chamomile, or fruit flavors. Embodiments comprise calming supplements such as L-Theanine.

Formulae for exemplary embodiments are provided in the following tables. Amounts are approximate. Each table provides a recipe for one batch of chews according to an aspect of the invention. In embodiments, the emulsifier is not included if the product only contains a food grade oil. In other embodiments, the emulsifier is necessary to combine water-based and oil based ingredients. For some embodiments medium-chain triglyceride (MCT) oil is not present in the chill chew, as it can have an energizing effect.

TABLE 1

| | Ingredient | Descriptor | Amount |
|---|---|---|---|
| 1 | Chai Concentrate (ginger, cinnamon, peppercorns, cardamom, and cloves) | Liquid (freshly brewed) | 8.2 oz. |
| 2 | Beet root | Powder | 0.6 oz. |
| 3 | C-Complex | Powder | Less than 0.1 oz |
| 4 | Sea Salt | Powder | 0.1 oz. |
| 5 | MCT Oil | Liquid | 0.6 oz. |
| 6 | Unflavored gelatin | Powder | 1.2 oz. |
| 7 | Collagen | Powder | 8.6 oz. |
| 8 | Lecithin | Powder | Less than 0.1 oz. |
| 9 | Baobab | Powder | 0.2 oz. |
| 10 | Coconut Milk | Powder | 1 oz. |
| 11 | Cocoa butter | Liquid | 0.8 oz. |
| 12 | Monk Fruit extract | Powder | Less than 0.1 oz. |
| 13 | Stevia | Powder | Less than 0.1 oz. |

TABLE 2

| | Ingredient | Descriptor | Amount |
|---|---|---|---|
| 1 | Cold Brew Coffee | Liquid (bottled) | 8.2 oz. |
| 2 | Cacao | Powder | 0.6 oz. |
| 3 | C-Complex | Powder | Less than 0.1 oz. |
| 4 | Sea Salt | Powder | 0.1 oz. |
| 5 | MCT Oil | Liquid | 0.6 oz. |
| 6 | Unflavored gelatin | Powder | 1.2 oz. |
| 7 | Collagen | Powder | 8.6 oz. |
| 8 | Lecithin | Powder | Less than 0.1 oz. |
| 9 | Baobab | Powder | 0.2 oz. |
| 10 | Coconut Milk | Powder | 1 oz. |
| 11 | Cocoa butter | Liquid | 0.8 oz. |
| 12 | Monk Fruit extract | Powder | Less than 0.1 oz. |
| 13 | Stevia | Powder | Less than 0.1 oz. |

TABLE 3

| | Ingredient | Descriptor | Amount |
|---|---|---|---|
| 1 | Lemon Concentrate | Liquid (bottled) | 4.3 oz. |
| 2 | Water | Liquid (tap) | 4.1 oz. |
| 3 | Lemon Oil | Liquid | 0.1 oz. |
| 4 | Sea Salt | Powder | 0.1 oz. |
| 5 | MCT Oil | Liquid | 0.6 oz. |
| 6 | Unflavored gelatin | Powder | 1.4 oz. |
| 7 | Collagen | Powder | 8.6 oz. |
| 8 | Lecithin | Powder | Less than 0.1 oz. |
| 9 | Baobab | Powder | 0.2 oz. |
| 10 | Coconut Milk | Powder | 1 oz. |
| 11 | Cocoa butter | Liquid | 0.8 fl. oz. |
| 12 | Turmeric | Liquid | Less than 0.1 fl. oz. |
| 13 | Monk Fruit extract | Powder | Less than 0.1 oz. |
| 14 | Stevia | Powder | Less than 0.1 oz. |
| 15 | C-Complex | Powder | Less than 0.1 oz. |

TABLE 4

| | Ingredient | Descriptor | Amount |
|---|---|---|---|
| 1 | Cold Brew Concentrate | Liquid | 2.2 oz. |
| 2 | Cacao | Powder | 0.5 oz. |
| 3 | C-Complex | Powder | 0.1 oz. |
| 4 | Sunflower Lecithin | Powder | Less than 0.1 oz. |
| 5 | MCT Oil | Liquid | 1.0 oz. |
| 6 | Unflavored Gelatin | Powder | 0.4 oz. |
| 7 | Collagen | Powder | 5.1 oz. |
| 8 | Coconut Milk | Powder | 0.5 oz. |
| 9 | Cocoa Butter | Solid | 0.4 oz. |
| 10 | Baobab | Powder | 0.1 oz. |
| 11 | Sea Salt | Powder | Less than 0.1 oz. |
| 12 | Stevia Extract | Powder | Less than 0.1 oz. |
| 13 | Monk Fruit Extract | Powder | Less than 0.1 oz. |

In one embodiment, all ingredients including flavoring (such as coffee concentrate), gelatin, cocoa butter, cacao, C-complex, sea salt, stevia extract, monk fruit extract, sunflower lecithin, MCT oil, coconut milk, and baobab) are mixed in a stainless steel stand mixer. The ingredients in the mixer are mixed until the mixture reaches 165° F. (approximately 74° C.). The collagen is then added to the above mixture and incorporated. The resulting mixture is rolled out, cut, and wrapped.

In another embodiment, unflavored gelatin is added to water and heated on low until dissolved. In one embodiment, the gelatin-water mixture is heated in a double boiler. The gelatin-water mixture may be heated to 181° F. (approximately 83° C.) to facilitate complete melting without degrading the gelatin proteins. Other ingredients, including flavoring agents, may then be added and blended well into the gelatin mixture. Finally, after heating, collagen is added to this mixture. The resulting mixture is poured into molds and frozen until hard. In other embodiments, while the chew needs to set before cutting and wrapping, it is not frozen.

Using a standard residential freezer to harden the mixture requires approximately 2 hours of chill time. One skilled in the art will appreciate that flash coolers and other systems may be employed to facilitate and speed the freezing process.

Once hardened, the chews can be released from the molds, cut to size, and wrapped. They may, in some embodiments, be refrigerated or vacuum sealed to preserve freshness until use.

The resulting chew is soft enough for those with weakened dentition, weak chewing ability, and osteoporosis to chew comfortably. Additionally, the resulting chew is non-sticky.

In one embodiment, a mixer is used to blend the collagen and other ingredients. Other methods may utilize a blender or other suitable system for blending and emulsifying ingredients.

One skilled in the art will appreciate that such a chew may also be a suitable delivery mechanism for other nutraceuticals or supplements including but not limited to beet powder, cacao, MCT oil, and turmeric.

The foregoing description of the embodiments of the invention has been presented for the purposes of illustration and description. Each and every page of this submission, and all contents thereon, however characterized, identified, or numbered, is considered a substantive part of this application for all purposes, irrespective of form or placement within the application. This specification is not intended to be exhaustive or to limit the invention to the precise form disclosed. Many modifications and variations are possible in light of this disclosure.

What is claimed is:

1. A system for delivery of collagen, said system consisting of:
    a chew, said chew consisting of a non-sticky gelatinous composition of matter, said matter consisting of:
        a gelatin base;
        an emulsifier if said chew includes a water-based liquid;
        a food grade oil; and
        collagen;
    wherein ingredients of said chew proportionately consist of:
        less than 0.1 oz. of C-complex;
        approximately 0.1 oz. of sea salt;
        approximately 0.6 oz. of medium-chain triglyceride (MCT) oil;
        approximately 1.2 or approximately 1.4 oz. of unflavored gelatin;
        approximately 8.6 oz. of said collagen;
        less than 0.1 oz. of lecithin;
        approximately 0.2 oz. of baobab;
        approximately 1 oz. of coconut milk;
        approximately 0.8 oz. of cocoa butter;
        less than 0.1 oz. of monk fruit extract;
        less than 0.1 oz. of stevia; and
        at least one of:
            approximately 8.2 oz. of chai concentrate, said chai concentrate comprising a liquid base, ginger, cinnamon, peppercorns, cardamom, and cloves, or approximately 0.6 oz. of beet root;
            or
            approximately 8.2 oz. of cold brew coffee or approximately 0.6 oz. of cacao;
            or
            approximately 4.3 oz. of lemon concentrate, approximately 4.1 oz. of water, approximately 0.1 oz. of lemon oil, or less than 0.1 oz. of turmeric;
    whereby said chew is a non-sticky gelatinous composition.

2. The system of claim 1 wherein said baobab consists of approximately 0.2 oz. of baobab powder.

3. The system of claim 1 wherein said chew consists of said approximately 8.2 oz. of the chai concentrate, and said approximately 0.6 oz. of beet root.

4. The system of claim 1 wherein said collagen has a collagen weight, said gelatin base comprises said unflavored gelatin, said unflavored gelatin has a gelatin weight, and there exists a collagen weight to gelatin weight ratio wherein said collagen weight to gelatin weight ratio is between 6 and 13.

5. The chewable supplement of claim 1, wherein said emulsifier is said less than 0.1 oz. of lecithin.

6. The chewable supplement of claim 1 wherein said gelatin and said collagen has a weight ratio between 1:5 and 1:15.

7. The chewable supplement of claim 1 wherein said chai concentrate is a brewed liquid.

8. The chewable supplement of claim 1 consisting of:
    said approximately 8.2 oz. of cold brew coffee; and
    said approximately 0.6 oz. of cacao.

9. The chewable supplement of claim 1 consisting of:
    said approximately 4.3 oz. of lemon concentrate;
    said approximately 4.1 oz. of water; and
    said approximately 0.1 oz. of lemon oil; and
    said less than 0.1 oz. of turmeric.

10. A chewable supplement, said chewable supplement consisting of:
    gelatin;
    collagen;
    and
    an emulsifier if said chew includes a water-based liquid;
    wherein ingredients of said chewable supplement proportionately consist of:
        approximately 0.1 oz. of C-complex;
        less than 0.1 oz. of sea salt;
        approximately 1.0 oz. of medium-chain triglyceride (MCT) oil;
        wherein said gelatin is approximately 0.4 oz. of unflavored gelatin;
        wherein said collagen is approximately 5.1 oz. of said collagen;
        less than 0.1 oz. of lecithin;
        approximately 0.1 oz. of baobab;
        approximately 0.5 oz. of coconut milk;
        approximately 0.4 oz. of cocoa butter;
        less than 0.1 oz. of monk fruit extract;
        less than 0.1 oz. of stevia;
        approximately 2.2 oz. of cold brew coffee concentrate; and
        approximately 0.5 oz. of cacao;
    whereby said chew is a non-sticky gelatinous composition.

11. The chewable supplement of claim 10 wherein said gelatin and said collagen has a weight ratio between 1:5 and 1:15.

12. The chewable supplement of claim 10 wherein said emulsifier is said approximately 0.1 oz. of said lecithin.

13. The chewable supplement of claim 10 wherein said collagen has a collagen weight, said gelatin base comprises said unflavored gelatin, said unflavored gelatin has a gelatin weight, and there exists a collagen weight to gelatin weight ratio wherein said collagen weight to gelatin weight ratio is between 6 and 13.

14. The chewable supplement of claim 10, wherein said lecithin is sunflower lecithin.

* * * * *